United States Patent [19]

Wallace

[11] Patent Number: 4,556,996
[45] Date of Patent: Dec. 10, 1985

[54] HEART VALVE

[75] Inventor: Robert S. Wallace, 823 S. Longwood Ave., Los Angeles, Calif. 90005

[73] Assignees: Robert S. Wallace, Los Angeles; Jack Bauman, Pacific Palisades, both of Calif. ; a part interest

[21] Appl. No.: 520,499

[22] Filed: Aug. 4, 1983

[51] Int. Cl.4 .............................................. A61F 1/22
[52] U.S. Cl. ....................................................... 623/2
[58] Field of Search ...................... 3/1.5; 137/849, 847

[56] References Cited

U.S. PATENT DOCUMENTS

| | | |
|---|---|---|
| 3,589,392 | 6/1971 | Meyer . |
| 3,717,883 | 2/1973 | Mosher ................................... 3/1.5 |
| 3,755,823 | 9/1973 | Hancock ................................. 3/1.5 |
| 3,861,416 | 1/1975 | Wichterle . |
| 3,938,197 | 2/1976 | Milo ........................................ 3/1.5 |

Primary Examiner—Richard J. Apley
Assistant Examiner—James Prizant
Attorney, Agent, or Firm—William W. Haefliger

[57] ABSTRACT

An artificial heart valve includes tapering flaps which are suspended to pivot between open and closed positions.

6 Claims, 5 Drawing Figures

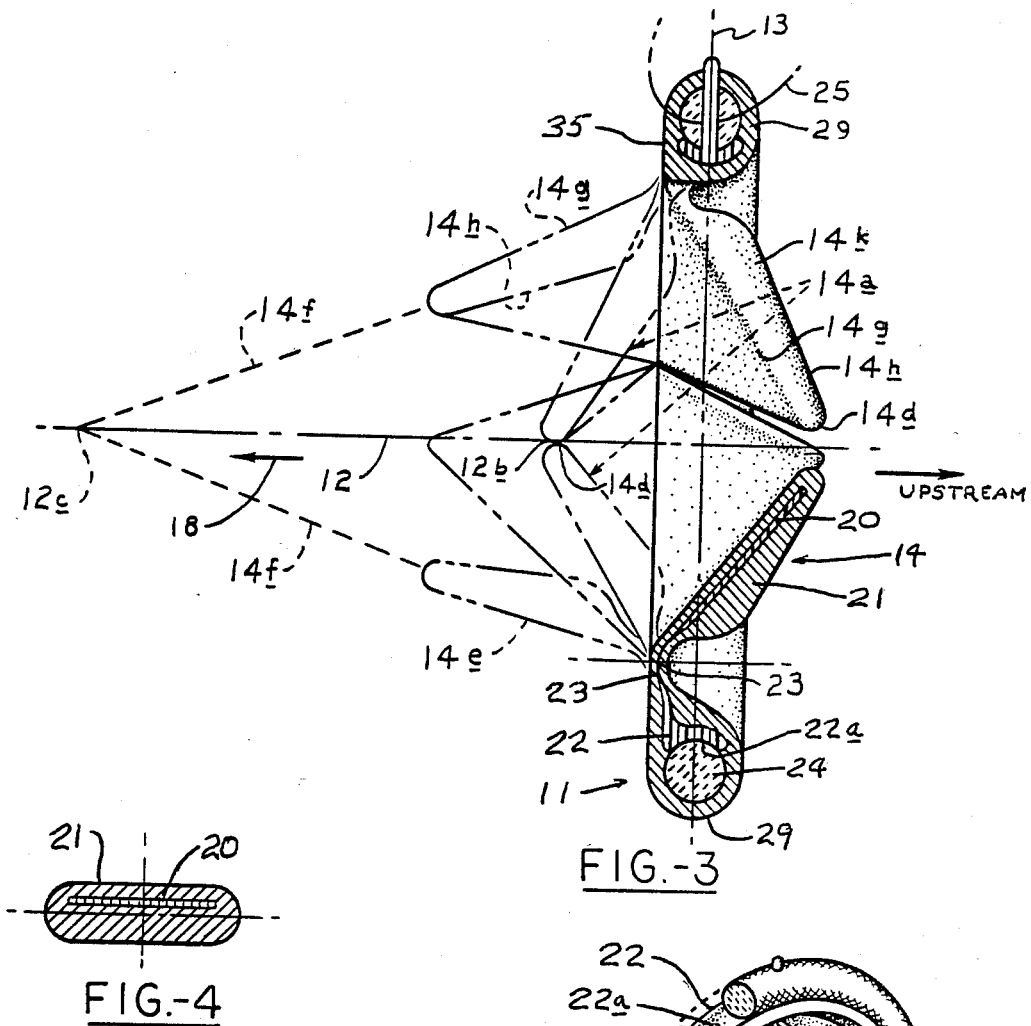
FIG.-3
FIG.-4
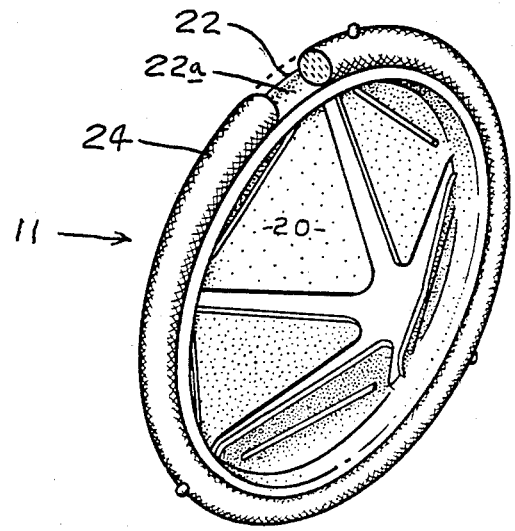
FIG.-5

HEART VALVE

BACKGROUND OF THE INVENTION

This invention relates generally to heart valves, and more particularly concerns improvements in check valves useful in cardiac surgery.

Cardiac surgery is now commonly accepted practice for replacement of defective mitral or aortal valves in the human heart. Replacement valves have included those of ball and cage and leaflet type. Difficulties and problems associated with prior artificial heart valves include backflow leakage, damage to blood cells, and clotting. Also, certain prior replacement valves have been regarded as insufficiently simulating the level of performance of the natural heart valve, its functioning and simplicity.

SUMMARY OF THE INVENTION

It is a major object of the invention to provide an artificial heart valve characterized as improving upon the performance of prior such valves, and by simplicity and ruggedness of construction.

Basically, the artificial valve of the invention comprises:

(a) an annular support having a central axis, (b) multiple flaps integrally connected with said support to yieldably flex between first and second positions, (c) the flaps tapering relatively away from the support and extending toward one portion of said axis in said first position in which the valve is substantially closed and characterized in that edges of adjacent flaps extend contiguously, (d) the flaps extending toward a second portion of said axis in said second position in which the valve is substantially fully open, and characterized in that edges of adjacent flaps are spread apart to openly pass blood flow therebetween.

As will appear, the flaps may consist of a molded elastomer as for example silicone rubber; the annular support may also consist of an elastomer molded integrally with the flaps; the two positions of the flaps are typically axially spaced apart at one side of a plane defined by the annular support; and the flaps may with unusual advantages have an as-molded position located at the opposite side of that plane. Accordingly, ease of molding, and yieldable return flexing toward closed (first) position of the flaps are both enabled.

In addition, the annular support may typically incorporate an non-elastomeric core ring of a construction and composition to desirably retain sutures; and the flaps may contain core hinges extending from the annular support. In practice there are at least four of such flaps, and preferably five flaps which are alike and equally spaced about the support axis. Accordingly, in flap second (open) position or positions, the edges of adjacent flaps define openings therebetween which flare in the direction toward the referenced second portion of the central axis, whereby the area of such openings plus the central open area at the tips of the flaps is enhanced for passing blood flow generally unidirectionally forward. Hinges provided by flap cores act to yieldably urge the flaps toward closed positions, yet allow flap displacement toward full open position during a blood flow pressure pulse.

These and other objects and advantages of the invention, as well as the details of an illustrative embodiment, will be more fully understood from the following description and drawings, in which:

DRAWING DESCRIPTION

FIG. 3 is a section on lines 3—3 of FIG. 1;

FIG. 4 is a section on lines 4—4 of FIG. 1; and

FIG. 5 is a perspective view of a pre-assembly of a plastic insert or core together with a core suture ring.

DETAILED DESCRIPTION

Figure 1:
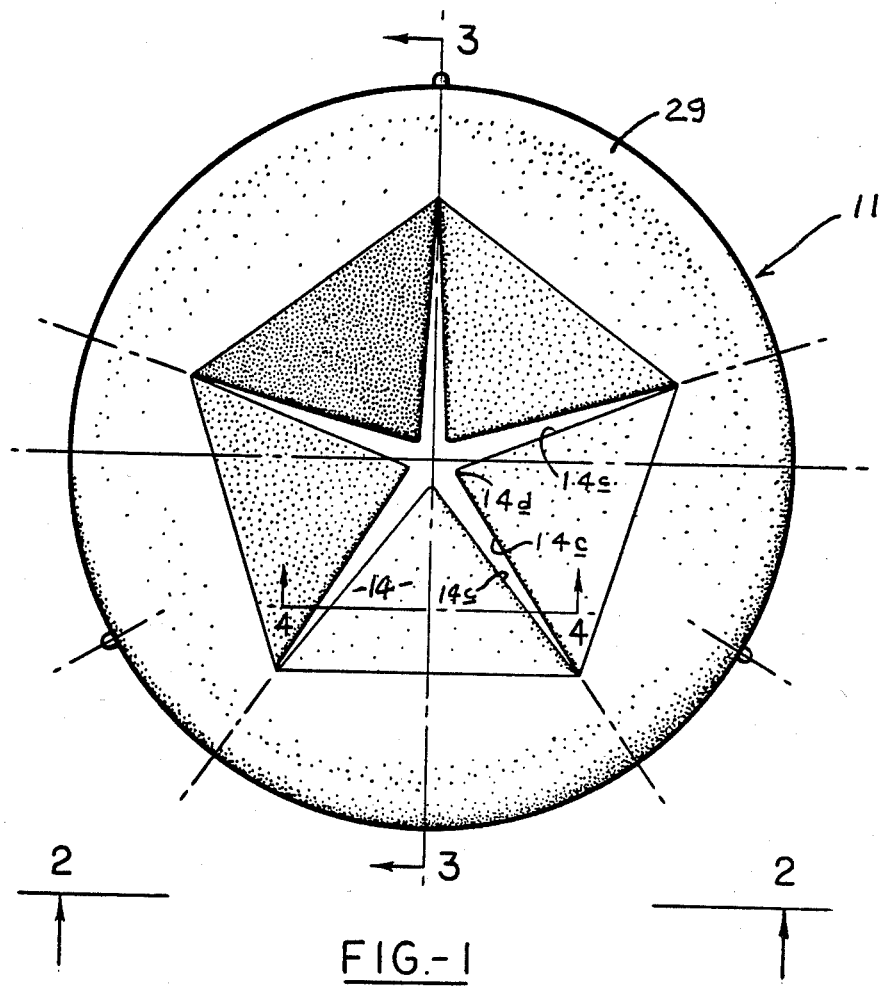
FIG. 1 is a frontal elevational view of an artificial heat valve embodying the invention.
Figure 2:
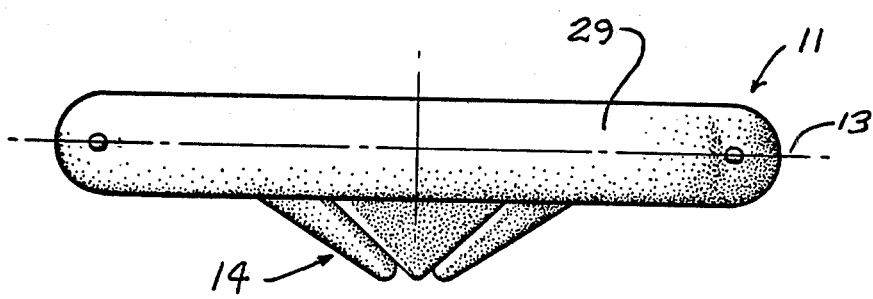
FIG. 2 is a top plan view taken on lines 2—2 of FIG. 1.

Referring first to FIGS. 1-4, the artificial heart valve 10 comprises an annular or ring shaped support 11 having a central axis 12 normal to the plane 13 of the support. The valve also includes multiple flaps 14 integrally connected with or to the support to yieldably flex between first and second positions. The flaps typically have generally triangular perimetral configurations or outlines and taper relatively away from the support annulus 11. Further, broken lines 14a indicate the flaps in said first positions in which the check valve is closed or substantially closed. That position is further characterized in that the flap tapering edges 14c extend contiguously, as for example in touching relation, and the flap tips 14d also extend contiguously in touching or near touching relation proximate a first portion 12b of axis 12. At least four flaps are provided, and preferably five are employed.

Broken lines 14e indicate the flaps in representative second positions in which the check valve is fully open to pass blood flow generally unidirectionally through the valve in the direction of arrow 18. The flap edges 14c in open position are spaced apart to pass blood flow therebetween; and, such edges define openings therebetween which flare in the direction toward a second portion 12c of the axis. Flaps 14 also extend toward axis second portion 12c, as indicated by broken lines 14f in FIG. 3.

The flaps are further characterized as essentially flat, and have opposite flat sides 14g and 14h which taper toward rounded tips 14d. Axis portions 12b and 12c are axially spaced apart, as shown, at one side of plane 13.

The flaps may advantageously have flat triangular cores indicated at 20 about which soft elastomeric material 21 is molded to give the flaps 14 their exterior shape as described above. Such cores 20 typically consist of molded plastic material, as for example DELRIN, CELCON, or equivalent material, to provide strength and rigidity. The annular support 11 may advantageously comprise a first core ring 22 to which flaps 14 are typically attached, as by hinged connection at 23 of flap cores 20 to the ring 22. Thus, the ring 22 and cores 20 may be molded as a unit to also provide the arcuate, thin hinges 23, as shown. The support 11 may also advantageously include a second core ring 24 mounted on the first ring 22, as for example in the annular rim recess 22a seen in FIGS. 3 and 5. Ring 24 may consist of woven fiber (as for example NYLON) to which sutures are connectible (see suture 25 in FIG. 3). The support 11 also includes an elastomer ring 29 molded about cores 22 and 24 and also molded integrally with flap material 21, to provide the smooth, arcuate contours as shown, so that damage to blood cells in all flap positions is minimized.

FIG. 3 also shows the flaps as having an as-molded-position indicated by lines 14k, and wherein the hinges 23 and flaps are not tensioned. To tension the hinges, the flaps after molding are displaced over center (i.e. through the annulus 11) into first positions 14a, wherein the flap edges engage one another to block further flap displacement toward the plane 13. The flap cores are thus yieldably tensioned in bending. As the flaps bend toward second positions 14e by the pressure of the flowing blood, the hinges are increasingly tensioned, for returning the flaps toward first positions 14a as the blood flow pressure pulse drops.

FIG. 1 shows the flaps in as-molded state. See also the flat side 35 of the valve to lay flatly against body tissue to which sutures 25 attach.

Other molded flap materials that are usable in view of human or animal body acceptance are: polycarbonate, polyethylene, polychromate, polypropylene, TEFLON, NYLON and DACRON.

I claim:

1. An artificial heart valve comprising:
   (a) a circular annular support having a central axis, said annular support having an imaginary bisecting plane of symmetry perpendicular to said axis,
   (b) multiple triangular valve flaps integrally molded with said flaps and support,
   (c) hinges having a thickness less than that of either the flaps or annular support and joining the flaps to the annular support on a first side of said symmetry plane,
   (d) each of said flaps having an unbiased as molded position in which each of said triangular flaps taper substantially to a point on said axis which is on a second side of said symmetry plane, each of said flaps further including a plastic core of resiliently bendable molded material which acts to urge the flaps toward their as molded position,
   (e) said valve in use being repositioned by inverting said flaps through said plane of symmetry so that they are biased to a first closed position, said flaps further being capable of opening to a second position when the pressure across the valve is sufficient to overcome the biasing of said flaps.

2. The combination of claim 1 wherein said annular support includes a non-elastomeric core ring to retain sutures.

3. The combination of claim 1 wherein there are at least four of said flaps.

4. The combination of claim 1 wherein said annular support includes a first plastic core ring, a second core ring on said first core ring and to which sutures are connectible, and an elastomer ring about said first and second core rings.

5. The combination of claim 4 wherein said elastomer consists of silicone rubber.

6. The combination of claim 1 in which there are five like flaps.

* * * * *